United States Patent [19]

Webinger et al.

[11] 4,258,874

[45] Mar. 31, 1981

[54] TWO PART CONTAINER HAVING ADJUSTABLE VENTS

[75] Inventors: George P. Webinger; David Adamek, both of Minneapolis, Minn.

[73] Assignee: Champion International Corporation, Stamford, Conn.

[21] Appl. No.: 70,243

[22] Filed: Aug. 27, 1979

[51] Int. Cl.³ .................. B65D 77/30; B65D 47/12
[52] U.S. Cl. ......................... 229/23 BT; 239/59; 229/4.5; 229/21
[58] Field of Search ............ 229/4.5, 5.5, 21, 23 BT; 239/59

[56] References Cited

U.S. PATENT DOCUMENTS

| 1,380,288 | 5/1921 | Holtschneider | 239/59 |
|---|---|---|---|
| 1,732,028 | 10/1929 | Reiner | 239/59 X |
| 1,733,571 | 10/1929 | Alden et al. | 229/4.5 |
| 1,916,519 | 7/1933 | Madsen et al. | 229/21 |
| 2,247,600 | 7/1941 | Bremmam et al. | 239/59 X |
| 2,438,129 | 3/1948 | Rich | 239/59 |
| 2,738,225 | 3/1956 | Meek | 239/59 X |
| 3,232,469 | 2/1966 | Piazze | 229/4.5 X |

FOREIGN PATENT DOCUMENTS

| 2322360 | 11/1973 | Fed. Rep. of Germany | 239/59 |
|---|---|---|---|
| 2231216 | 12/1974 | France | 239/59 |

Primary Examiner—Davis T. Moorhead
Attorney, Agent, or Firm—Evelyn M. Sommer

[57] ABSTRACT

A two part paperboard container having adjustable vents is described and is intended for use with a sublimable composition. The container consists of an inner tubular member and an outer tubular sleeve member both of a truncated conical configuration. The inner tubular member, which is adapted to receive the sublimable composition, is in turn disposed within the outer sleeve member. The outer surface of the inner member is in frictional engagement with the inner surface of the outer sleeve member which functions to seal the carton. The inner member may be rotated relative to the outer sleeve member to at least partially align die cuts, provided in the walls of the tubular members, thereby exposing the composition to the air enabling it to sublime. Continued relative rotation of the tubular members will reset the die cuts in a nonaligned position thereby resealing the container. A portion of the inner member which projects above the upper edge of the outer sleeve member may be readily grasped to facilitate the relative rotation of the tubular members.

7 Claims, 8 Drawing Figures

TWO PART CONTAINER HAVING ADJUSTABLE VENTS

The subject invention relates to a new and improved paperboard container having adjustable vents for use with a sublimable material such as an air freshener or insecticide. More particularly, the subject invention consists of a two part tapered tubular container, wherein the inner tube, containing the sublimable material, is disposed within an outer tubular sleeve. The inner tubular member is frictionally engaged with the outer sleeve and is capable of rotation along its longitudinal axis relative to the outer sleeve. Die cuts or vents are provided in the side walls of both the inner and outer members. By rotating the inner member relative to the outer sleeve these die cuts may be at least partially aligned such that the composition sealed within the inner member is exposed to air thereby enabling the composition to sublime. The sublimation process may be substantially reduced by further rotating the inner member to a position such that the respective die cuts in the tubes are nonaligned, thereby resealing the composition with the tubes.

Containers for sublimable materials in the prior art were generally formed from a molded plastic and had a plurality of air vents therein. To prevent unwanted sublimation of the product after the product was inserted into the plastic containers and until such time as the product was purchased by the consumer, the containers were wrapped in a plastic sealer. When the consumer purchased the container, he would unwrap the plastic thereby irreversibly starting the sublimation process. Should the consumer wish to conserve the product for use only at such times when it is needed, he would have to attempt to rewrap the package to prevent the continual sublimation of the product. The rewrapping of the product is not only difficult, but in addition forced the consumer to handle a potentially poisonous composition.

Accordingly, it is an object of the subject invention to provide a container for a sublimable product having adjustable vents such that the process of sublimation can be regulated.

It is a further object of the subject invention to provide a container having adjustable vents that is easy and safe to use.

It is another object of the subject invention to provide a container, for a sublimable material having adjustable vents, which is formed from a paperboard material, thereby reducing manufacturing costs.

Accordingly, there is provided a container formed from a paperboard material which consists of an inner tapered tubular member and an outer tapered tubular sleeve member. The inner and outer members have a generally truncated conical configuration wherein the base of the inner member has a diameter slightly less than the diameter of the base of the outer sleeve member. The inner member is disposed within the outer sleeve, with the outer surface of the inner member being in frictional engagement with the inner surface of the outer sleeve member. The inner member may be rotated along its longitudinal axis relative to the outer sleeve member. At least one die cut portion or vent is provided in the side walls of both the inner and outer members. More specifically, the outer sleeve member is provided with a die cut which is at least as large as the die cut formed in the inner member. By rotating the inner member relative to the outer member, the respective die cuts may be aligned as more fully described below.

In accordance with the subject invention, the inner member is sealed at the upper end thereof, and after the manufacturer places the sublimable material into the inner member, the lower end of the container is then sealed. The positioning of the inner member, relative to the outer member which places the die cuts in a nonaligned position, functions to seal the container so that it may be shipped, displayed and stored. After purchasing the product, the consumer merely has to rotate the inner member relative to the outer sleeve member such that the respective die cuts of the members are at least partially aligned thereby exposing the stored product to the air enabling it to sublime. Further, should the consumer wish to substantially reduce or stop the sublimation process, he may again rotate the tubular members relative to each other until the die cut portions do not overlap thereby sealing the sublimable material from the air. Further objects and advantages of the subject invention will become apparent from the following detailed description, taken in conjunction with the drawings in which:

Figure 8:
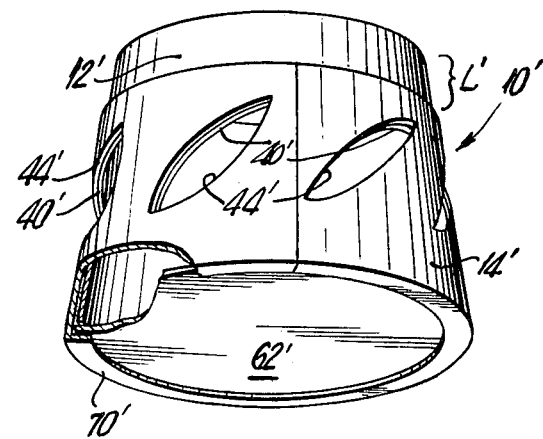

FIG. 8 is a perspective view partially cut away as viewed from the bottom of the erected container of the second embodiment of the subject invention and illustrating the opened position of the container. Referring to FIGS. 1–4, the container of the subject invention is designated generally by the numeral 10, and is intended for use as an aesthetically pleasing, adjustably vented holder for a sublimable material such as an insecticide or an air freshener. The container 10 consists of an inner tubular member 12 and an outer sleeve member 14.

Figure 1:
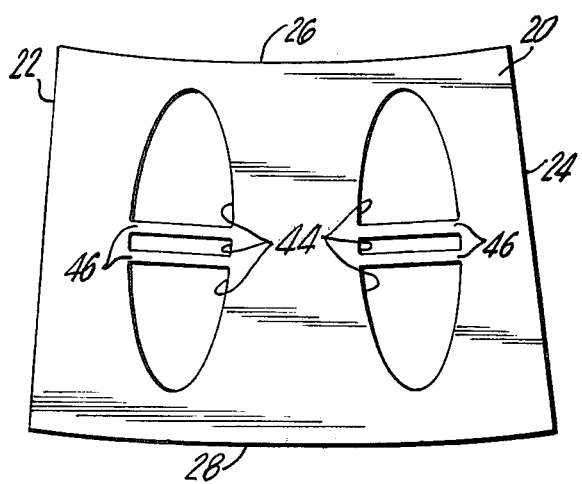
FIG. 1 is a plan view of the blank adapted to be folded into the outer sleeve member of a first embodiment of a container of the subject invention.
Figure 2:
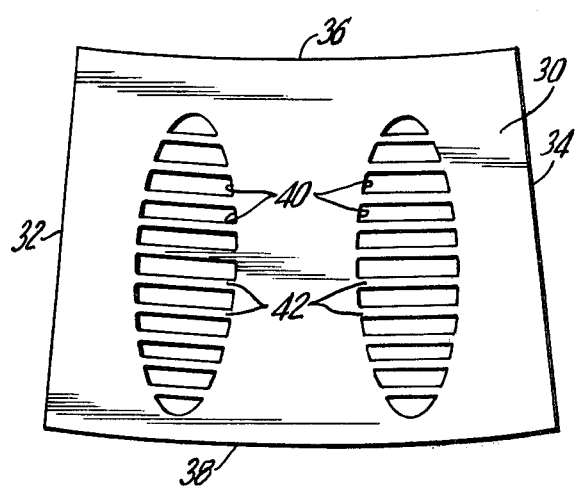
FIG. 2 is a plan view of the blank adapted to be folded into the inner member of a first embodiment of a container of the subject invention.

As illustrated more particularly in FIG. 1, the blank 20 for forming the outer sleeve member 14 has tapered side edges 22 and 24 and arcuate top and bottom edges 26 and 28 such that when the blank is folded, a truncated conical configuration is obtained. Similarly, as illustrated in FIG. 2, the blank 30 for forming the inner member 12 of the subject invention is provided with tapered side edges 32 and 34 and arcuate top and bottom edges 36 and 38. The length of the top arcuate edge 36 of the blank 30 is slightly shorter than the length of the top edge 26 of the blank 20. Further, the lower edge 38 of the blank 30 is correspondingly shorter than the length of the bottom edge 28 of the blank 20. By this arrangement, the inner tubular member 12, formed from blank 30, has a slightly smaller diameter than the outer sleeve member 14, formed from blank 20, such that the inner member 12 can be received within the outer sleeve member 14 as more fully described hereinafter. By having the lengths of the top and bottom edges 36, 38 of the blank 30 only slightly shorter than the respective top and bottom edges 26, 28 of the blank 20, a frictional engagement is obtained in the erected container 10 between the outer surface of the inner member 12 and the inner surface of the outer sleeve member 14, which functions to seal the container 10.

The blank 30 for forming the inner member 12 of the subject invention is provided with at least one die cut portion or vent. As illustrated in FIG. 2, a plurality of die cuts 40 are provided which approximate the configuration of an upright, sectioned oval. Rib sections 42 between the individual sectioned die cut portions 40 function to maintain the structural integrity of the blank 30.

Blank 20 for forming the outer sleeve member 14 of the subject invention is provided with die cuts, indicated generally as 44, which also approximate the configuration of a sectioned oval. Rib sections 46 are similarly provided in blank 30 for maintaining the structural integrity of the blank 30. The die cuts 44 are located in blank 20 in generally the same spatial relationship as the die cuts 40 are located in blank 30 except that the die cuts 46 are spaced farther away from the bottom edge 28 of blank 20 than the die cuts 40 of blank 30 are spaced from bottom edge 38. By this arrangement, and as more fully described hereinafter, accurate registration of die cuts 40, 44 in the erected container may be obtained when the inner member 12 is aligned in a specific position relative to the outer sleeve member 14. To permit sufficient ventilation of the product held within the container 10, die cuts 44 should have an area at least as large as the area of the die cuts 40 formed in blank 30. The particular size and shape of the die cuts formed in the blanks may vary in accordance with aesthetic considerations and the amount of ventilation required.

Figure 3:
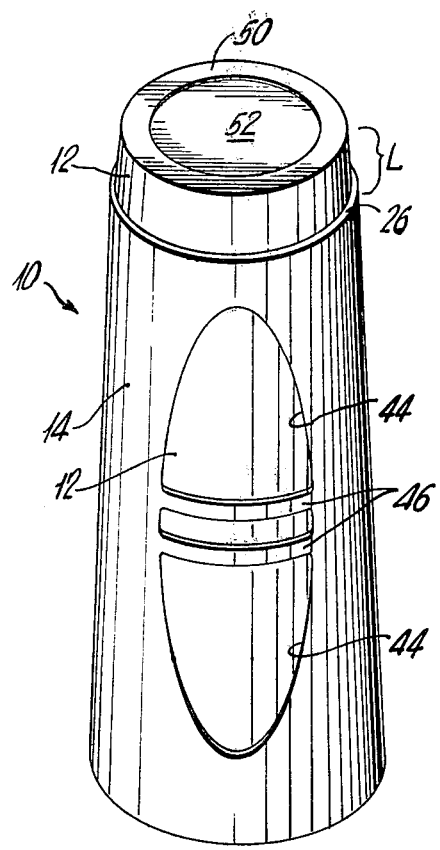
FIG. 3 is a perspective view of the first embodiment of the erected container of the subject invention in the closed position.
Figure 4:
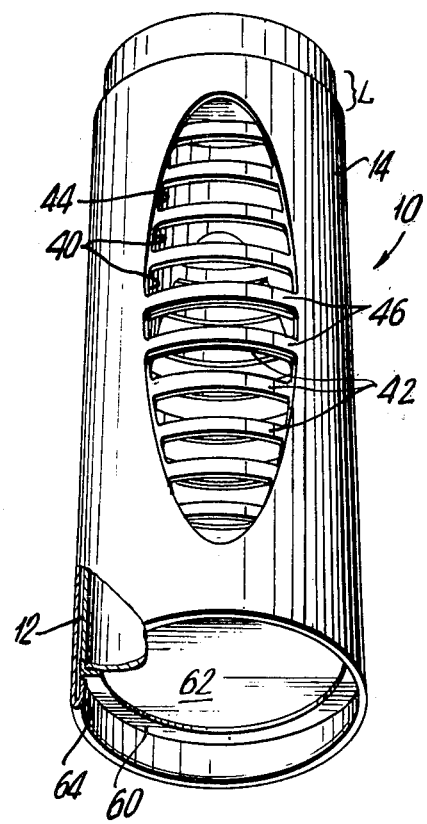
FIG. 4 is a perspective view partially cut away as viewed from the bottom of the first embodiment of the erected container of the subject invention in the opened position.
Figure 5:
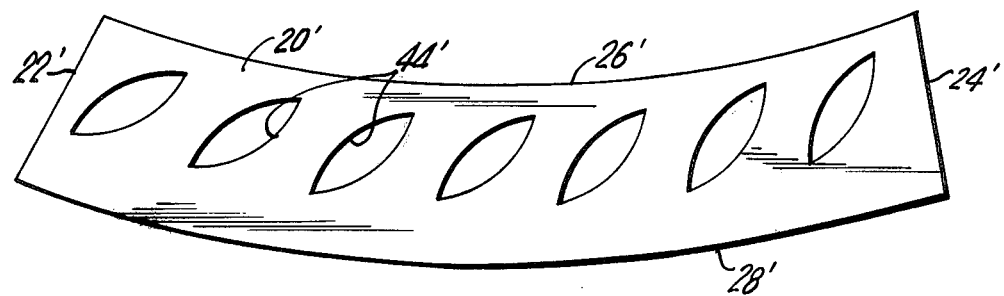
FIG. 5 is a plan view of the blank adapted to be folded into the outer member of the container of a second embodiment of the subject invention.
Figure 6:
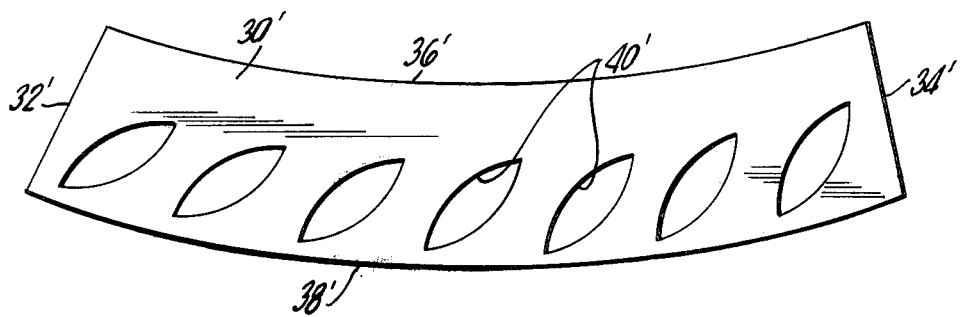
FIG. 6 is a plan view of the blank adapted to be folded into the inner member of the container of a second embodiment of the subject invention.

In forming the container 10 of the subject invention, the blank 30 is curled about its longitudinal axis such that side edge 32 may be adhesively joined to side edge 34 thereby forming a tapered truncated conical configuration. In a preferred embodiment, and as illustrated in FIG. 3, the top edge 36 of inner member 12 is rolled inwardly such that an annular ring 50 is formed which extends inward and perpendicularly from the side walls of inner member 12. A generally circular cover member 52 may then be adhesively attached to the inner surface of the annular ring 50 thereby sealing the upper portion of the inner member 12. At this time, a sublimable product (not shown) may be inserted and then sealed within the inner member 12. As illustrated in FIG. 4, the bottom edge 38 of the inner member 12 is folded inwardly creating an annular ring 60 similar to the annular ring 50 at the top edge of inner member 12. A generally circular base member 62 may then be adhesively joined to the annular ring 60 thereby sealing the inner member 12 and the product within.

The blank 20 may be formed into the outer sleeve member 14 by curling the blank 20 about its longitudinal axis such that the side edge 22 may be adhesively joined to the side edge 24 thereby forming the tapered truncated conical configuration of the outer sleeve member 14. The inner member 12 is then inserted through the open lower end of the outer sleeve member 14 and moved upwardly therein until a protion L of the inner member 12 emerges from the top of outer member 14 and a frictional engagement between the members 12, 14 is obtained. The difference in lengths between the top edges and the bottom edges of blanks 20, 30 (resulting in the difference in diameters of the members 12, 14) controls the point at which a frictional engagement between the members 12, 14 occurs and therefore affects the extent to which the inner member 12 projects above the outer member 14. To insure that the die cuts 40, 44 will be properly aligned, the distance between the bottom of the die cuts 44 and the bottom edge 28 of the blank 20 is greater than the distance between the bottom edge of the die cuts 40 from the bottom edge 38 in blank 30. By this arrangement, the die cuts 40 of inner member 12 may be aligned with die cuts 44 of outer member 14 even though a portion L of inner member 12 extends a distance above the top edge of outer member 14.

As illustrated in FIG. 4, the lower edge 38 of the outer member 14 is curled upwardly forming a U-shaped support member 64 for holding the inner member 12 within the outer member 14. The U-shaped member 64 functions to maintain the internal positioning of the inner member 12 relative to the outer sleeve member 14 such that a secure frictional engagement is obtained between the outer surface of the inner member 12 and the inner surface of the outer sleeve member 14 thereby sealing the product within the container. To minimize the inadvertent sublimation of the product while it is being stored, shipped and displayed, it is necessary that the die cuts 40 and 44 of the inner member 12 and the outer sleeve member 14 be in a non-aligned position. As illustrated in FIG. 3, when the die cuts 40 and 44 are in a non-aligned position, the product within the inner member 12 is not exposed to the air and the frictional engagement between the tubular members 12 and 14 functions to seal the product within the container 10.

When the consumer wishes to activate the product, he merely has to rotate the inner member 12 relative to the outer member 14 thereby at least partially aligning the die cuts 40 and 44 as illustrated in FIG. 4. Rotation of the inner member 12 is readily accomplished by grasping and turning the inner member 12 at portion L which projects above the top edge of the outer sleeve member 14. Should the consumer want to halt the sublimation process, the inner member can be further rotated relative to the outer member 14 such that the die cuts 40 and 44 are no longer aligned (as in FIG. 3). By this arrangement, the product stored inside the inner member 12 is again sealed from exposure to the air, and the sublimation process is greatly reduced.

A second embodiment of the subject invention is illustrated in FIGS. 5 through 8. Blank 20' for forming outer sleeve member 14' of the subject invention is provided with tapered side edges 22', 24', as well as arcuate top and bottom edges 26', 28'. Blank 20' is further provided with a plurality of generally eliptically shaped die cuts 44' spaced along the length of the blank 20'. Blank 30' is similarly provided with tapered side edges 32', 34', and arcuate top and bottom edges 36' and 38'. Generally elliptically shaped die cuts 40' are spaced along the length of the blank 30'. As in the first embodiment, the distance between the bottom of die cuts 40' and the bottom edge 38' of the blank 30' is less than the distance between the bottom edge of the die cuts 44' and the bottom edge 28' of blank 20'. In addition, the length of top arcuate edge 36' of blank 30' is slightly shorter than the length of top edge 26' of blank 20' and similarly bottom edge 38' is slightly shorter than the length of bottom edge 28'.

In erecting the container, blank 30' is curled about its longitudinal axis such that side edge 32' may be adhesively joined to side edge 34' thereby forming inner member 12' having a generally truncated conical configuration. The upper edge 36' is rolled inwardly forming an annular ring 50' which extends perpendicularly inward from the top edge of the blank 30'. A generally circular cover member 52' is adhesively joined to annular ring 50' thereby sealing the top of the inner member 12'. Outer sleeve member 14' is formed by curling blank 20' about its longitudinal axis such that side edge 22' may be adhesively joined to side edge 24'.

An alternate method of sealing the bottom end of the container 10' of the subject invention is illustrated in FIG. 8. While two methods of sealing the container are illustrated it is intended that any sealing method known in the art be covered within the scope of this invention. In the second embodiment, prior to the insertion of the product into the inner member 12', the inner member 12' is inserted into the inner sleeve member 14'. As in the first embodiment, the inner member 12' is inserted until a frictinal engagement is obtained between the outer surface of inner member 12' and the inner surface of outer member 14'. Since the inner member 12' has a diameter less than the diameter of outer sleeve member 14', a portion L' of the inner member 12' will extend above the upper edge of outer sleeve member 14'. The product (not shown) may then be inserted within the inner member 12' and thereafter the bottom edge of outer sleeve member 14' is rolled inwardly forming an annular ring 70' which extends perpendicularly inward from the side thereof. A circular base member 62' may then be adhesively joined to the annular ring 70' thereby sealing the bottom of the container 10'. By this arrangement, the bottom edge 38' of the inner member 12' rests on the generally circular base 62' thereby sealing the product within the container. The annular ring 70' further functions to maintain the position of the inner member 12' within the outer sleeve member 14'.

As in the first embodiment, the die cuts 40' are positioned in blank 30', in a spatial relationship similar to the positioning of the die cuts 44' in blank 20'. Also as in the first embodiment, the die cuts 40' are spaced a shorter distance from the bottom edge 38' of the inner member 12' then the die cuts 44' are spaced from the bottom edge 28' of the outer sleeve member 14'. By this arrangement, the die cuts 40', 44' may be aligned in the erected container 10' even though the top edge of the inner member 12' projects above the top edge of the outer sleeve member 14'.

Figure 7:
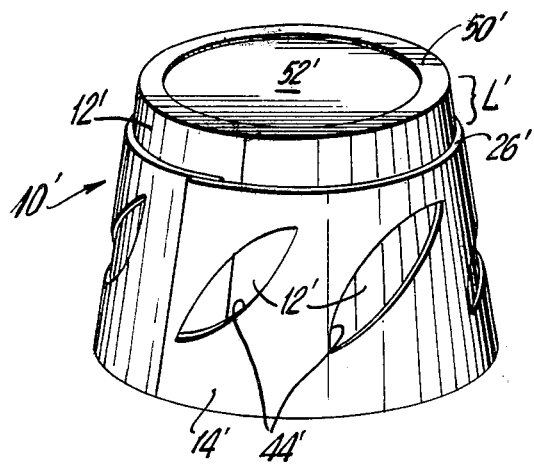
FIG. 7 is a perspective view as viewed from the top of the erected container of the second embodiment of the subject invention in the closed position of the container.

During shipment display and storage of the container, to prevent the inadvertent sublimation of the product within the container 10', the die cuts are positioned in a non-aligned relationship as illustrated in FIG. 7. To initiate the sublimation process, the consumer has to merely grasp the portion L' of inner member 12' extending above the upper edge of the outer sleeve member 14' and rotate the inner member 12' such that the die 40' and 44' are at least partially aligned. By this arrangement, the product may be exposed to the air via the aligned die cuts thereby permitting the product to sublimate. The bottom edge 38' of inner member 12' is in slidable contact with the base 62' as the inner member 12' is being rotated. Should the consumer wish to halt the sublimation of the product he may continue to rotate the inner member 12' until the die cuts are once again in a non-aligned position thereby sealing the product within the container 10'.

Accordingly, there is provided a new and improved paperboard container having adjustable vents for use with a sublimable material. The container consists of an inner member and an outer sleeve member both of truncated conical configuration. The inner member, containing the sublimable material is frictionally engaged with the outer sleeve member and is capable of rotation along its longitudinal axis relative to the outer sleeve. Die cuts or vents are provided in the side walls of both the inner and outer members and by rotating the inner member relative to the outer sleeve member these vents may be at least partially aligned such that the composition sealed within the inner member is exposed to the air enabling the composition to sublime. Further, the sublimation process may be reduced by again rotating the inner member to a position such that the respective die cuts in the members are non-aligned, thereby resealing the product within the container.

Although the subject carton has been described by reference to a preferred embodiment, it is apparent that other modifications could be devised by those skilled in the art that would fall within the scope and spirit of the present invention as defined by the appended claims.

What is claimed is:

1. A two part paperboard container having adjustable vents, for holding a solid sublimable composition comprising:

an inner tubular member of generally truncated, conical configuration and having at least one die cut portion in the wall thereof, said inner tubular member being adapted to receive said solid composition;

means for sealing the upper end of said inner tubular member;

an outer tubular sleeve member of generally truncated, conical configuration, with the base of said outer sleeve member having a diameter larger than the diameter of the base of said inner member, said outer sleeve member having at least one die cut portion in the wall thereof, with said inner tubular member being disposed within said outer sleeve member and capable of rotation therein about the longitudinal axes of said members;

means for sealing the lower end of said container; and means for holding said inner tubular member within said outer sleeve member such that a frictional engagement is obtained between the outer surface of said inner tubular member and the inner surface of said outer sleeve member, whereby when said inner tubular member is rotated relative to said outer sleeve member, the respective die cuts of said members may be at least partially aligned such that the solid composition within said inner tubular member is exposed to the air thereby enabling the composition to sublime, wherein said means for holding said inner tubular member within said outer sleeve member includes an annular support member formed from rolling the bottom edge of said outer sleeve member into an upturned U-shaped configuration such that the bottom edge of said inner tubular member rests on the upturned bottom edge of said outer sleeve member and is supported thereby.

2. A two part paperboard container as recited in claim 1 wherein the die cut portion in said outer sleeve member is at least as large as the die cut portion in said inner tubular member.

3. A two part paperboard container having adjustable vents for holding a solid sublimable composition comprising:

an inner tubular member of generally truncated, conical configuration and having at least one die cut portion in the wall thereof, said inner tubular member being adapted to receive said solid composition, said inner tubular member including an upper annular ring formed by rolling the top edge of said inner tubular member perpendicularly inward, said inner tubular member further including a generally circular cover member which is adhesively joined to said upper annular ring thereby sealing the upper end of said inner tubular member, and with said inner tubular member including a lower annular ring formed by rolling the bottom edge of said inner tubular member perpendicularly inward, said inner tubular member further including a generally circular base member which is adhesively joined to said lower annular ring thereby sealing the lower end of the inner tubular member;

an outer tubular sleeve member of generally truncated, conical configuration, with the base of said outer sleeve member having a diameter larger than the diameter of the base of said inner member, said outer sleeve member having at least one die cut portion in the wall thereof, said die cut portion of said outer sleeve member being at least as large as the die cut portion of said inner tubular member, with said inner tubular member being disposed within said outer sleeve member and capable of rotation therein about the longitudinal axes of said members, said inner tubular member projecting above the upper edge of said outer sleeve member thereby providing a gripping area for rotating the inner tubular member relative to the outer sleeve member, said outer sleeve member further including an annular support member formed from rolling the bottom edge of said outer sleeve member into an upturned U-shaped configuration such that the bottom edge of said inner tubular member rests on the upturned bottom edge of said outer sleeve member and is supported thereby such that a frictional engagement is obtained between the outer surface of said inner tubular member and the inner surface of said outer sleeve member, whereby when said inner tubular member is rotated relative to said outer sleeve member the respective die cuts of said members may be at least partially aligned such that the solid composition within said inner tubular member ia exposed to the air thereby enabling the composition to sublime.

4. A two part paperboard container as recited in claim 3 wherein said tubular members are provided with a plurality of die cuts disposed to form a sectioned oval configuration with the areas between said die cuts defining ribs, said ribs for increasing the structural integrity of said tubular members.

5. A two part paperboard container having adjustable vents for holding a solid sublimable composition comprising:

an inner tubular member of generally truncated conical configuration and having at least one die cut portion in the wall threof, said inner tubular member being adapted to receive said solid composition, said inner tubular member including an upper annular ring formed by rolling the top edge of said inner tubular member perpendicularly inward, said inner tubular member further including a generally circular cover member which is adhesively joined to said upper annular ring thereby sealing the upper end of said inner tubular member; and an outer tubular sleeve member of generally truncated, conical configuration, with the base of said outer sleeve member having a diameter larger than the diameter of the base of said inner member, said outer sleeve member having at least one die cut portion in the wall thereof, said die cut portion of said outer sleeve member being at least as large as the die cut portion of said inner member, with said inner member being disposed within said outer sleeve member and capable of rotation therein about the longitudinal axes of said members, said inner tubular member projecting above the upper edge of said outer sleeve member thereby providing a gripping area for rotating the inner tubular member relative to the outer sleeve member, and with said outer tubular member including a lower annular ring formed from rolling the bottom edge of said outer sleeve member perpendicularly inward, said outer sleeve member further including a generally circular base member adhesively joined to said lower annular ring thereby sealing the lower end of said container and providing a support for said inner tubular member such that a frictional engagement is obtained between the outer surface of said inner member and the inner surface of said outer sleeve member, whereby when said inner tubular member is rotated relative to said outer sleeve member, the respective die cuts of said members may be at least partially aligned such that the solid composition within said inner tubular member is exposed to the air thereby enabling the composition to sublime.

6. A two part paperboard container as recited in claim 5 wherein said tubular members are provided with a plurality of die cuts, said die cuts being of a generally elliptical configuration.

7. A two part paperboard container having adjustable vents, for holding a solid sublimable composition comprising:

an inner tubular member of generally truncated, conical configuration and having at least one die cut portion in the wall thereof, said inner tubular member being adapted to receive said solid composition;

means for sealing the upper end of said inner tubular member;

an outer tubular sleeve member of generally truncated, conical configuration, with the base of said outer sleeve member having a diameter larger than the diameter of the base of said inner member, said outer sleeve member having at least one die cut portion in the wall thereof, with said inner tubular member being disposed within said outer sleeve member and capable of rotation therein about the longitudinal axes of said members;

means for sealing the lower end of said container; and means for holding said inner tubular member within said outer sleeve member such that a frictional engagement is obtained between the outer surface of said inner tubular member and the inner surface of said outer sleeve member, whereby when said inner tubular member is rotated relative to said outer sleeve member, the respective die cuts of said members may be at least partially aligned such that the solid compositon within said inner tubular member is exposed to the air thereby enabling the composition to sublime, wherein the means for sealing the lower end of said container and the means for holding said inner tubular member within said outer sleeve member includes a lower annular ring formed from rolling the bottom edge of said outer sleeve perpendicularly inward, said means further including a generally circular base member adhesively joined to said lower annular ring, such that the bottom edge of said inner tubular member is supported by said circular base member.

* * * * *